US00PP20376P2

(12) United States Plant Patent
van Niekerk

(10) Patent No.: US PP20,376 P2
(45) Date of Patent: Oct. 6, 2009

(54) ***HEBE* PLANT NAMED 'FROZEN FLAME'**

(50) Latin Name: ***Hebe* hybrid**
Varietal Denomination: Frozen Flame

(75) Inventor: Johan van Niekerk, Waddinxveen (NL)

(73) Assignee: Rolini BV (I.O.), Hazerswoude (NL)

( * ) Notice: Subject to any disclaimer, the term of this patent is extended or adjusted under 35 U.S.C. 154(b) by 0 days.

(21) Appl. No.: 12/220,988

(22) Filed: Jul. 30, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—Annette H Para
(74) *Attorney, Agent, or Firm*—Penny J. Aguirre

(57) ABSTRACT

A new cultivar of *Hebe,* 'Frozen Flame', characterized by its vigorous growth habit, its narrow, variegated foliage with green-gray centers and white margins that is suffused with purple in cool temperatures in spring, and its free flowering habit with racemes of lavender flowers for 6 to 8 weeks in mid summer into autumn.

2 Drawing Sheets

Botanical classification: *Hebe* hybrid.
Cultivar designation: 'Frozen Flame'.

BACKGROUND OF THE INVENTION

The present invention relates to a new and distinct cultivar of *Hebe,* botanically of hybrid origin and known as *Hebe* 'Frozen Flame' and will be referred to hereafter by its cultivar name, 'Frozen Flame'. 'Frozen Flame' is grown for use as a container plant and as a landscape shrub.

The new cultivar was discovered as a chance seedling in the inventor's nursery in spring of 2004 in Waddinxveen, The Netherlands. The parentage is unknown as the inventor grows over 30 cultivars of *Hebe.* Based on foliage characteristics, it is suspected that *Hebe* 'Heartbreaker' (not patented) may be one of the parents.

Asexual reproduction of the new cultivar was first accomplished by the inventor using terminal stem cuttings in Waddinxveen, The Netherlands in 2004. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Frozen Flame' as a new and distinct cultivar of *Hebe.*

1. 'Frozen Flame' exhibits a very vigorous growth habit.
2. 'Frozen Flame' exhibits foliage that is variegated with green-gray centers and white margins that is suffused with purple in cool temperatures in early spring.
3. 'Frozen Flame' exhibits long leaves.
4. 'Frozen Flame' exhibits racemes of lavender flowers in mid summer into autumn.

'Frozen Flame' can be most closely compared to 'Heartbreaker' and another chance seedling discovered by the inventor 'Magic Summer' (U.S. Plant patent application Ser. No. 12/221,004). In comparison to 'Heartbreaker', 'Frozen Flame' has foliage with narrower margins and centers that are gray-green rather than green, has longer leaves and is more floriferous as 'Heartbreaker' rarely produces flowers. In comparison to 'Magic Summer', 'Frozen Flame' has longer leaves, is less compact and taller in height, is more vigorous, has slightly darker lavender flowers and develops purple foliage coloration about a month earlier in spring.

BRIEF DESCRIPTION OF THE DRAWING

The accompanying colored photographs illustrate the overall appearance and distinct characteristics of the new *Hebe.* The photographs were taken of a plant approximately one year in age as grown in a one-gallon container outdoors in Waddinxveen, The Netherlands.

The photograph on the first sheet is a side view of 'Frozen Flame', the photograph on the top of the second sheet provides a close-up view of the spring foliage of 'Frozen Flame', and the photograph on the bottom of the second sheet provides a close-up view of the flowers of 'Frozen Flame'.

The colors in the photographs are as close as possible with the photographic and printing technology utilized. The color values cited in the detailed botanical description accurately describe the colors of the new *Hebe.*

DETAILED BOTANICAL DESCRIPTION OF THE PLANT

The following is a detailed description of one year-old plants of the new cultivar as grown outdoors in one gallon containers in Waddinxveen, The Netherlands. Plants were grown under average day temperatures of 10° to 20° C. and average night temperatures of 1° to 11° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General plant characteristics:

*Plant type.*—Perennial shrub.

*Plant habit.*—Bushy, upright and spreading.

*Flowering period.*—For 6 to 8 weeks from mid summer into autumn in The Netherlands.

*Height and spread.*—Reaches about 43 cm in height and 80 cm in width in a one gallon container and 60 to 70 cm in height and 1 m in width in 3 years when grown in the garden.

*Hardiness.*—Tolerates temperatures at least from −5° C. to 35° C. and is cold hardy to at least U.S.D.A. Zone 7.

*Disease resistance.*—No particular susceptibility or resistance to diseases has been observed.

*Root description.*—Fibrous and fine.

*Growth rate.*—Vigorous, about 17 cm per growth season, a flowering plant is produced in about 4 months.

*Propagation.*—Terminal stem cuttings.

Stem description:

*Stem size.*—Lateral branches are an average of 17.3 cm in length and 3 mm in width.

*Stem shape.*—Round.

*Stem color.*—N200A.

*Stem surface.*—Moderately glossy, smooth.

*Internode length.*—Average of 1.1 cm.

*Branching habit.*—Freely branched from base, average of 24 lateral branches.

Foliage description:

*Leaf shape.*—Narrow oblanceolate to narrow oblong.

*Leaf division.*—Simple.

*Leaf base.*—Cuneate.

*Leaf apex.*—Broadly acute.

*Leaf venation.*—Pinnate, only mid rib is conspicuous, 147A to 189A on upper surface and 147A on lower surface.

*Leaf margins.*—Entire, occasionally have one small tooth on each side near apex.

*Leaf attachment.*—Sessile.

*Leaf arrangement.*—Opposite.

*Leaf surface.*—Glabrous and satiny on upper and lower surface, leathery texture.

*Leaf color.*—Upper surface summer foliage; centers 147A flushed with 189A, margins 150D to 154D, lower surface summer foliage; centers 147A flushed with 189A, margins 154C to 154D, winter/early spring upper surface; centers N186C to 200A, margins 186A, winter/early spring lower surface; centers 200B to 200C, margins 186A.

*Leaf number.*—Average of 32 (16 pairs) per lateral branch.

*Leaf size.*—Average of 3.5 cm in length and 6 mm in width.

*Leaf aspect.*—Held nearly horizontal to lateral branch.

*Leaf fragrance.*—None.

Flower description:

*Inflorescence type.*—Racemes of campanulate flowers, primarily terminal on lateral branches.

*Inflorescence size.*—Average of 6.3 cm in length (excluding peduncle) and 2.1 cm in width.

*Flower shape.*—Campanulate.

*Flower fragrance.*—None.

*Flower quantity.*—Average of 200 per raceme, average of 30 racemes in a one gallon container.

*Flower arrangement.*—Packed tightly in a whorl on peduncle with flowers opening from the base towards the apex.

*Flower aspect.*—Held outward.

*Flower lastingness.*—Individual flowers last about 7 days, 20% to 30% of flowers of the raceme are open at one time, self cleaning.

*Flower size.*—Average of 8 mm in depth and 9 mm in diameter.

*Peduncles.*—Strong, average of 6 cm in length and 1.5 mm in width, 1200B to 200C in color, surface is moderately glossy and smooth, round in shape, held at about a 35° angle to stem.

*Pedicels.*—Average of 3 mm in length and 0.5 mm in width, held at about a 35° angle to peduncle, 200C tinged with 147A in color, surface is glabrous.

*Flower buds.*—Elliptic in shape, average of 4 mm in length and 1.75 mm in diameter, 85C to 85D in color on upper side and 86C to 86D in color on lower side and blushed at apex with N155A with calyx portion 145B.

*Calyx.*—Rotate, average of 3 mm in length and 2 mm in width.

*Sepals.*—4, narrowly ovate in shape, margin is entire, apex is acute, base is fused on lower 30%, surface is glabrous and dull, color of upper and lower surface when opening is 145B, color of upper and lower surface when fully open 145A with margins 154D, average of 3 mm in length and 1 mm in width.

*Corolla.*—Campanulate with lower 50% of petal portion fused towards base.

*Petals.*—4, about 6 mm in length and 2 to 3.5 mm in width, lobes oblanceolate in shape, entire margins, apex of lobes obtuse, upper and lower surface is glabrous, color of upper surface when opening and fully open; 86B with throat N155A, color of lower surface when opening and fully open; 86D with fused base N155A, color of both surfaces after fading; 86C to 86D.

Reproductive organs:

*Gynoecium.*—1 Pistil, stigma is clavate in shape and N78B in color, style is about 5.8 mm in length and N78B to N78C in color, ovary is 144D to N144B in color.

*Androcoecium.*—2 stamens, anthers are elliptic in shape, about 1.75 mm in length and N186C in color, and dorsifixed, filaments are about 6 mm in length and N155A in color, pollen is minimal in quantity and 4D in color.

*Fruit and seed.*—Seed production has not been observed.

It is claimed:

1. A new and distinct cultivar of *Hebe* plant named 'Frozen Flame' as herein illustrated and described.

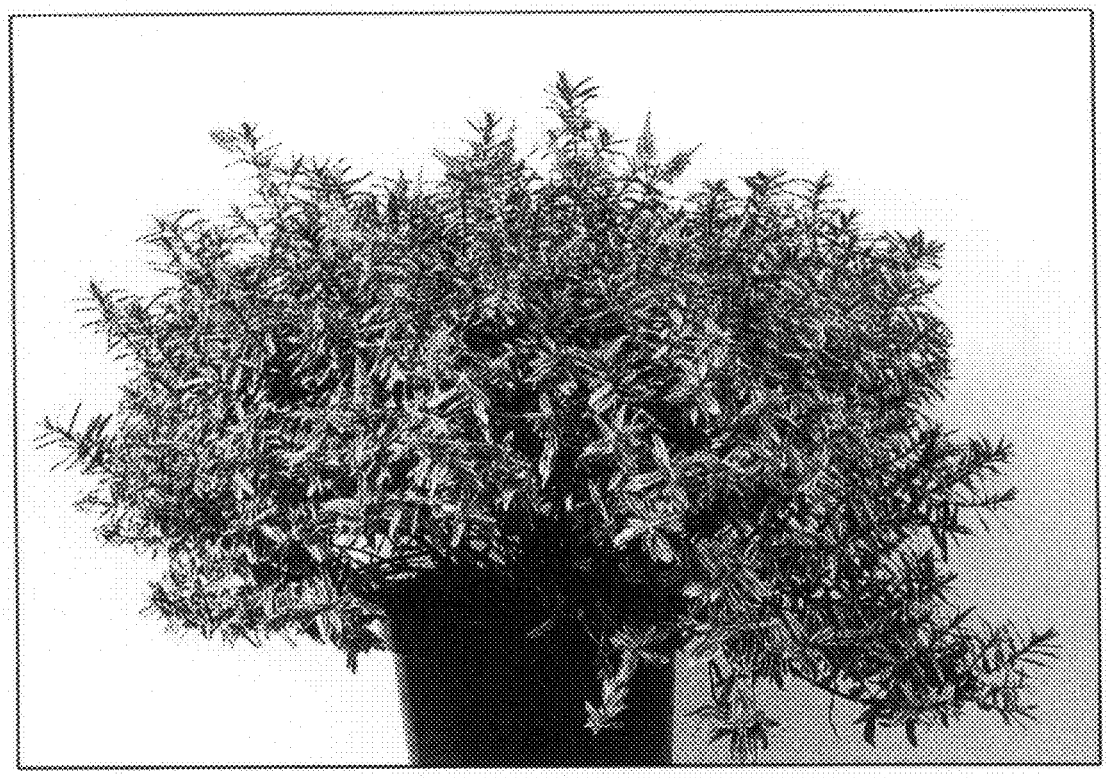

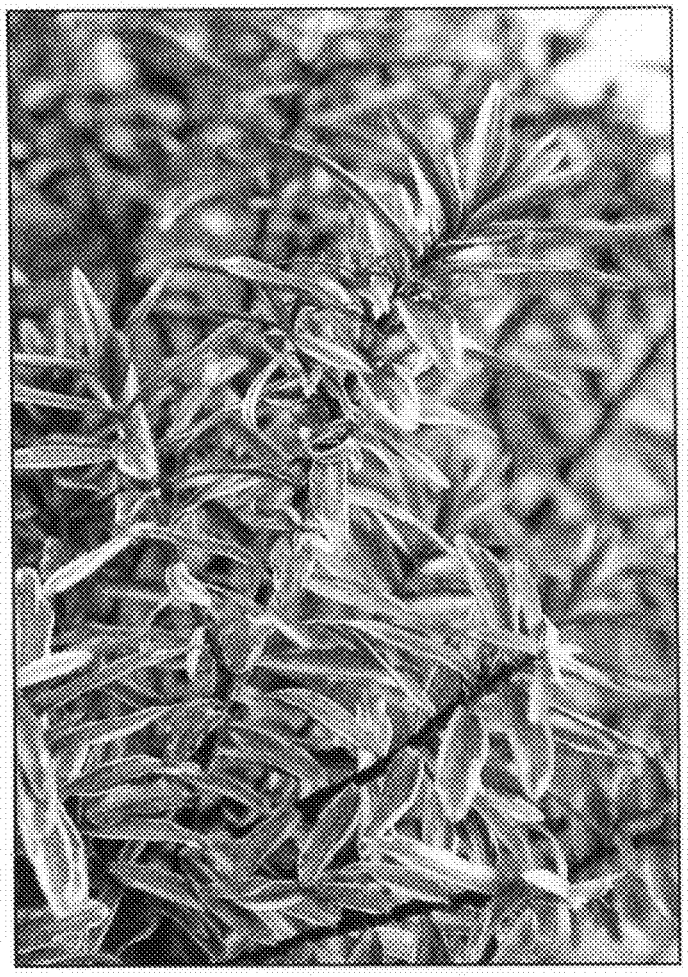
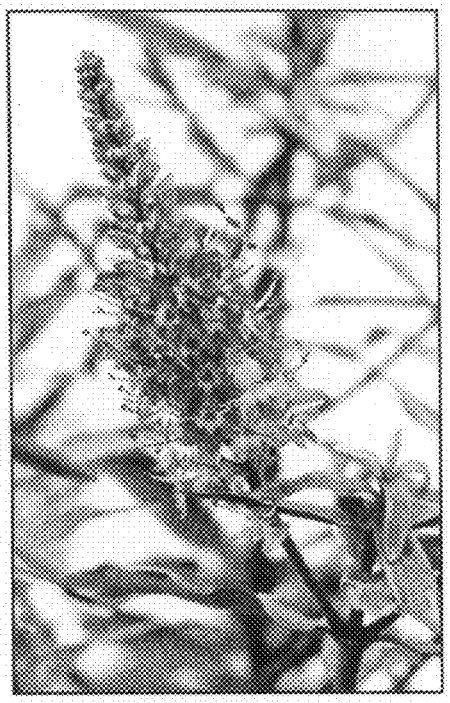

* * * * *